United States Patent [19]
Ichinose et al.

[11] Patent Number: 5,463,667
[45] Date of Patent: Oct. 31, 1995

[54] INSPECTION METHOD FOR SOLDERED JOINTS USING X-RAY IMAGING AND APPARATUS THEREFOR

[75] Inventors: Toshiaki Ichinose, Yokohama; Takanori Ninomiya, Hiratsuka; Asahiro Kuni, Setagaya; Kozo Nakahata, Chigasaki; Toshimitsu Hamada; Toshihiko Ayabe, both of Yokohama, all of Japan

[73] Assignee: Hitachi, Ltd., Tokyo, Japan

[21] Appl. No.: 53,240

[22] Filed: Apr. 28, 1993

[30] Foreign Application Priority Data

Apr. 30, 1992 [JP] Japan .................... 4-111337

[51] Int. Cl.⁶ ............................................. G01N 23/04
[52] U.S. Cl. ................................. 378/58; 378/210
[58] Field of Search .................................... 378/58

[56] References Cited

U.S. PATENT DOCUMENTS

| | | | |
|---|---|---|---|
| 4,809,308 | 2/1989 | Adams et al. | 378/58 |
| 4,910,757 | 3/1990 | Kiyasu | 378/58 |

FOREIGN PATENT DOCUMENTS 2-138855  5/1990  Japan .
4-105050  4/1992  Japan .

*Primary Examiner*—Craig E. Church
*Attorney, Agent, or Firm*—Antonelli, Terry, Stout & Kraus

[57] ABSTRACT

A method and an apparatus for inspecting a soldered joint with an X-ray, the soldered joint being formed by soldering a lead to a surface of a substrate. The method may include moving the substrate so as to move the surface of the substrate in an XY plane to position the soldered joint at a desired position in the XY plane, rotating the substrate so as to rotate the surface of the substrate in the XY plane to position the soldered joint at a desired orientation in the XY plane, rotating an X-ray source and a detector about the soldered joint in both of two mutually perpendicular planes perpendicular to the XY plane while maintaining the X-ray source and the detector at fixed positions relative to each other to establish a desired oblique irradiation angle between an X-ray from the X-ray source and the lead on the surface of the substrate, irradiating the soldered joint with the X-ray from the X-ray source at the desired oblique irradiation angle such that the X-ray is transmitted through the soldered joint and the substrate, detecting the X-ray transmitted through the soldered joint and the substrate with the detector, the detector producing an output signal indicative of the detected X-ray, and determining a condition of the soldered joint based on the output signal of the detector. The apparatus may operate in the same fashion.

6 Claims, 8 Drawing Sheets

FIG. 3a 
(SOP)

FIG. 3b 
(QFP)

FIG. 3c 
(MSP)

FIG. 3d 
(QFJ)

FIG. 3e 
(LCC)

FIG. 4a 
(SOP)

FIG. 4b 
(QFJ)

FIG. 4c 
(MSP)

FIG. 4d 
(LCC)

FIG. 11d
PRIOR ART

INSPECTION METHOD FOR SOLDERED JOINTS USING X-RAY IMAGING AND APPARATUS THEREFOR

BACKGROUND OF THE INVENTION

(1) Field of the Invention

The present invention relates to an inspection method for a soldering condition using X-ray imaging of electronic parts with mounted on a substrate by soldering with their leads so as to determine the soldering conditions of the leads soldered to the substrate based on a transmitted X-ray image in a preferable condition.

(2) Description of the Prior Art

With recent trends toward reduction in size and high density mounting of electronic parts on a printed circuit board, the use of electronic parts of the surface mounted device type (an electronic part which is mounted on a substrate by soldering its leads without using through holes) has gradually increased. In accordance with the above described tendency, a soldered joint of a lead on a surface of the substrate also has exhibited a gradual tendency to become small in size. As for a an inspection method for soldering condition of the small sized soldered joint, an inspection method for soldered joints using X-ray imaging as disclosed in JP-A-2-138855 (1990), for example, has gradually become widely used.

The inspecting method for a soldered portion using an X-ray imaging is briefly explained hereinafter.

When an X-ray is projected to a soldered portion, images corresponding to solder and leads in an X-ray image are detected darker than other portions because the solder and the leads have larger absorption coefficients for the X-ray than the substrate, and since the transmission path of the X-ray is longer in the solder and the leads than in other portions, the X-ray is absorbed more in the solder and the leads than in the other portions. Consequently, an excess or a lack of the solder can be determined by judging a condition of brightness or darkness of the X-ray image corresponding to the soldered portion. Especially, for electronic parts which are mounted on a surface of substrate by soldering their leads, whether the soldering condition is perfect or defective is clearly revealed in a quantity of the solder at a portion called a heel under the lead's standing portion. Accordingly, a defective condition of the soldering is easily determined by judging a condition of brightness or darkness in an X-ray image corresponding to the heel.

For an example, an electronic part having leads with a relatively large pitch size such as 1.27 mm pitch or 0.8 mm pitch has large size leads, and consequently a quantity of solder existing at a soldered joint between the lead and the surface of the substrate becomes inevitably large. And thickness of the existing solder in a perfect condition differs remarkably from the thickness of the existing solder in a defective condition. Accordingly, even if the standing portion of the lead is detected as an image superimposed on the image of the solder, the difference between the thickness of the solder in the perfect condition and in the defective condition appears relatively large in an X-ray image, and an effect of the standing portion of the lead becomes negligible in the judgement of the defective soldering condition.

However, in accordance with the current trend of high density mounting of electronic parts on a substrate, the pitch of the leads has become small and the quantity of the solder for soldering joints has decreased remarkably. For instance, a thickness of the soldering joint of an electronic part having 0.5 mm lead pitch is almost ½, and that of one having 0.3 mm lead pitch is almost ⅓, of the electronic part having 0.8 mm lead pitch. In accordance with the decrease in the thickness of the soldering joint as above described, the effect of the standing portion of the lead which is detected as an image superimposed on the image of the soldering joint is no longer negligible in the inspection of the soldered joint using X-ray imaging.

But, in accordance with the prior art inspecting method for a soldered joint disclosed in JP-A-2-138855 (1990), an X-ray is projected to the substrate from an oblique direction merely in order to avoid superimposing respective images of soldering joints at a front surface and a back surface of the substrate, and consequently consideration of an inclination of a standing portion of the lead and other factors is insufficient and a soldering condition of the soldered joint cannot be determined preferably.

Figure 11A:
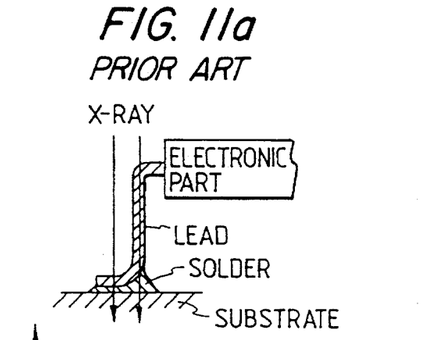
FIGS. 11a, 11b, 11c, and 11d are illustrations for explaining an inspection method for soldered joints relating to the prior art.
Figure 11B:
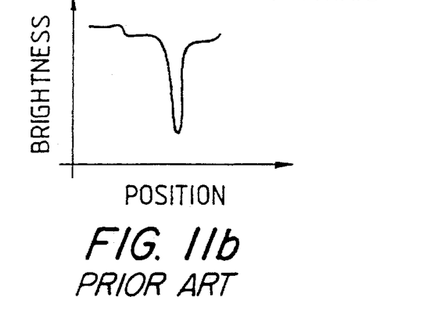
Figure 11C:
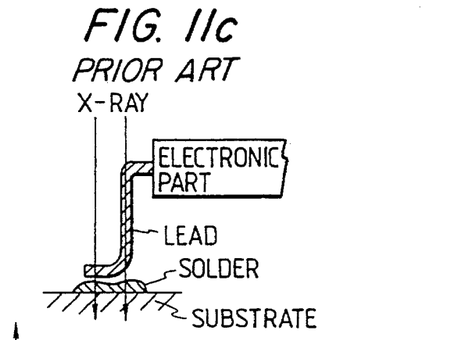
Figure 11D:
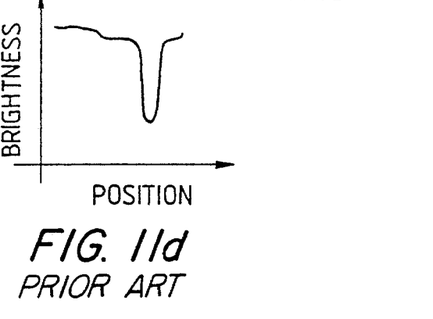

Furthermore, detected wave shapes of X-ray images are indicated in FIGS. 11b and 11d for a case when the soldered joints exist only at the front surface of the substrate and an X-ray is projected to the soldered joints from above the substrate. A difference between the detected wave shape FIG. 11b for a perfect soldering condition which is shown in FIG. 11a and the detected wave shape in FIG. 11d for a defective soldering condition which is shown in FIG. 11b is scarcely visible. Accordingly, when a small soldering joint is inspected by the above described inspecting method, a transmitting path of the X-ray through the standing portion of the lead is longer than that at the other portion of the lead, and an image at the standing portion of the lead superimposes on an image at the soldering portion. Consequently, features showing the soldering condition are scarcely visible in the X-ray image at the standing portion of the lead, and the judgement of whether the soldering condition is perfect or defective becomes difficult.

Furthermore, as another prior-art method, an inspection method for a micronized soldering portion is disclosed in JP-A-4-105050 (1992). In accordance with the prior art, an X-ray is irradiated to a soldering portion of a lead of an electronic part mounted on a surface of a substrate while almost continuously changing an incident angle to the soldering portion, and subsequently an intensity signal of the penetrated X-ray is detected corresponding to each change of the incident angle, a curve which expresses an amount of the penetrated or absorbed X-ray which passes through a point of a heel portion of the lead and spreads radiately, as a function of an angle θ around the point of the heel portion is derived from the detected intensity signals, and the quality of the soldering portion of the lead is determined from the curve. However, the above prior art has a problem that the inspection method according to the prior art requires a long time for the inspection because the detection of the intensity signal of the penetrated X-ray must be performed several times even for one soldering portion of the lead, for instance, nine times if the incident angle θ of the X-ray varies from 40° to 120° and the intensity signal of the penetrated X-ray is detected at every 10°.

SUMMARY OF THE INVENTION

(1) Objects of the Invention

The first object of the present invention is to provide an inspection method for soldered joints using X-ray imaging which can determine a soldering condition of leads of electronic parts soldered to a substrate when each of the electronic parts is mounted on a surface of the substrate by soldering to narrow-pitch leads in a preferable condition, and an apparatus therefore.

The second object of the present invention is to provide an inspection method for soldered joints using X-ray imaging which can determine a soldering condition of leads of electronic parts soldered to a substrate in a short time when each of the electronic parts is mounted on a surface of the substrate by soldering to narrow-pitch leads in a preferable condition, and an apparatus therefore.

(2) Methods for Solving the Problems

The above first object can be realized basically by detecting an X-ray transmitted through soldered joint as an X-ray image under a condition that the X-ray is projected obliquely to the lead standing portion in order to reveal a fraction contributed by the solder itself to a brightness change in the detected X-ray image while suppressing a fraction contributed by the lead.

And, as for an apparatus for inspecting soldered joints using X-ray imaging, the object can be realized by an apparatus comprising at least a θXY stage which moves the substrate on which electronic parts are mounted in X, Y directions and rotates the substrate in a horizontal plane for placing the substrate at a predetermined position, and a X-ray irradiation-detection system in which an X-ray source and an X-ray detector are maintained at fixed positions relative to each other while being rotated about a soldered joint in two vertical planes which cross each other at a right angle, wherein an X-ray from the X-ray source transmitted through the soldered joints is detected by the X-ray detector as an X-ray image under a condition that the X-ray is projected obliquely to the standing portion of the leads.

The above second object can be realized by arranging a plurality of X-ray irradiation detecting systems in directions corresponding to different lead alignments so as to reveal the fraction contributed by the solder itself to a brightness change in the detected X-ray image while suppressing the fraction contributed by the lead, selecting an X-ray irradiation detecting system arranged in the direction corresponding to the lead alignment which relates to the soldered joints currently being inspected, and detecting an X-ray transmitted through the soldered joints with an X-ray detector as an X-ray image under a condition that the X-ray is projected obliquely to the standing portion of the leads.

And, as for an apparatus for inspecting soldered joints using X-ray imaging, the object can be realized by an apparatus comprising at least the θXY stage which moves the substrate on which electronic parts are mounted in X, Y directions and rotates the substrate in a horizontal plane for placing the substrate at a predetermined position, a plurality of X-ray irradiation/detection systems each including an X-ray source and an X-ray detector which are maintained at fixed positions relative to each other while being rotated about a soldered joint in two vertical planes which cross each other at a right angle, wherein an X-ray from the X-ray source transmitted through the soldered joints is detected by the X-ray detector as an X-ray image under a condition that the X-ray is projected obliquely to the standing portion of the leads, and means for selecting one of the X-ray irradiation/detection systems arranged in a direction corresponding to a lead alignment which relates to soldered joints presently being inspected.

In a case when the X-ray transmitted through a soldered joint is detected as an X-ray image under a condition that the X-ray is projected obliquely to the standing portion of the lead, an absorption of the X-ray by the leads can be suppressed to a small amount. Accordingly, the fraction contributed by the solder itself to the brightness change in the detected X-ray image is revealed, while the fraction contributed by the leads is suppressed. Consequently, the soldering condition of the soldered joint can be determined preferably based on the detected X-ray image.

DETAILED DESCRIPTION OF THE EMBODIMENTS

Referring to FIGS. 1a to 1d and 2 to 10, embodiments of the present invention will be explained hereinafter.

First, a theory of the inspection method for soldered joints using X-ray imaging relating to the present invention will be explained referring to FIGS. 1a to 1d.

Figure 1A:
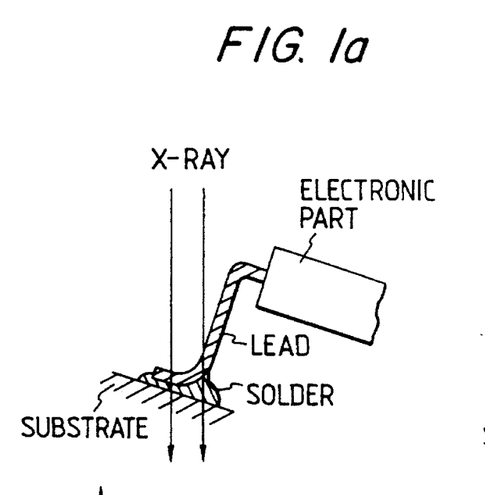
FIGS. 1a, 1b, 1c, and 1d are illustrations for explaining a theory of the inspection method for soldered joints based on detecting an X-ray image relating to the present invention.
Figure 1B:
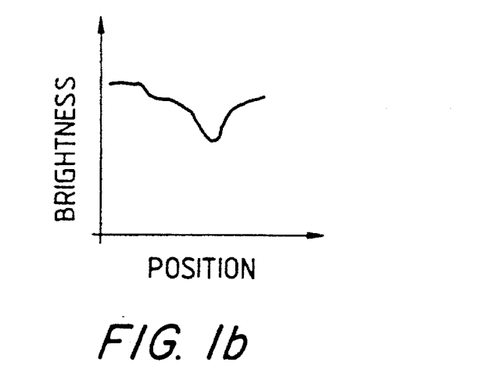
Figure 1C:
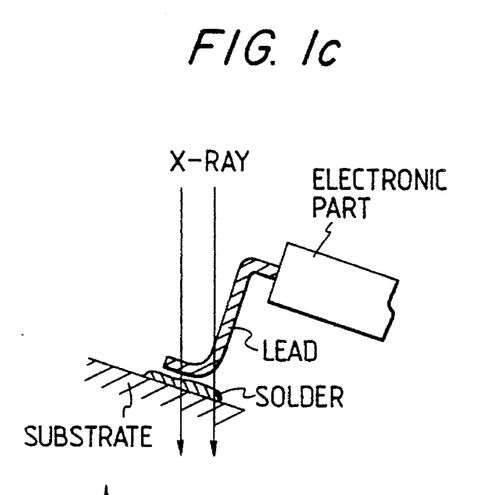
Figure 1D:
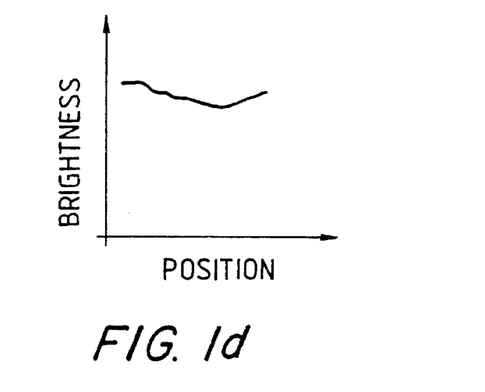

FIGS. 1a and 1c indicate a perfect soldering condition and a defective soldering condition, respectively, and FIGS. 1b and 1d show corresponding detected wave shapes of X-ray images. As the above figures show, an X-ray is projected to a soldered joint not in a direction parallel to the standing portion of the lead, but rather in a direction oblique to the standing portion of the lead. In accordance with the above irradiation of the X-ray, the X-ray is not absorbed very much by the standing portion of the lead but is greatly absorbed by the solder, and consequently the soldering condition can be determined clearly from the detected X-ray image.

Figure 2:
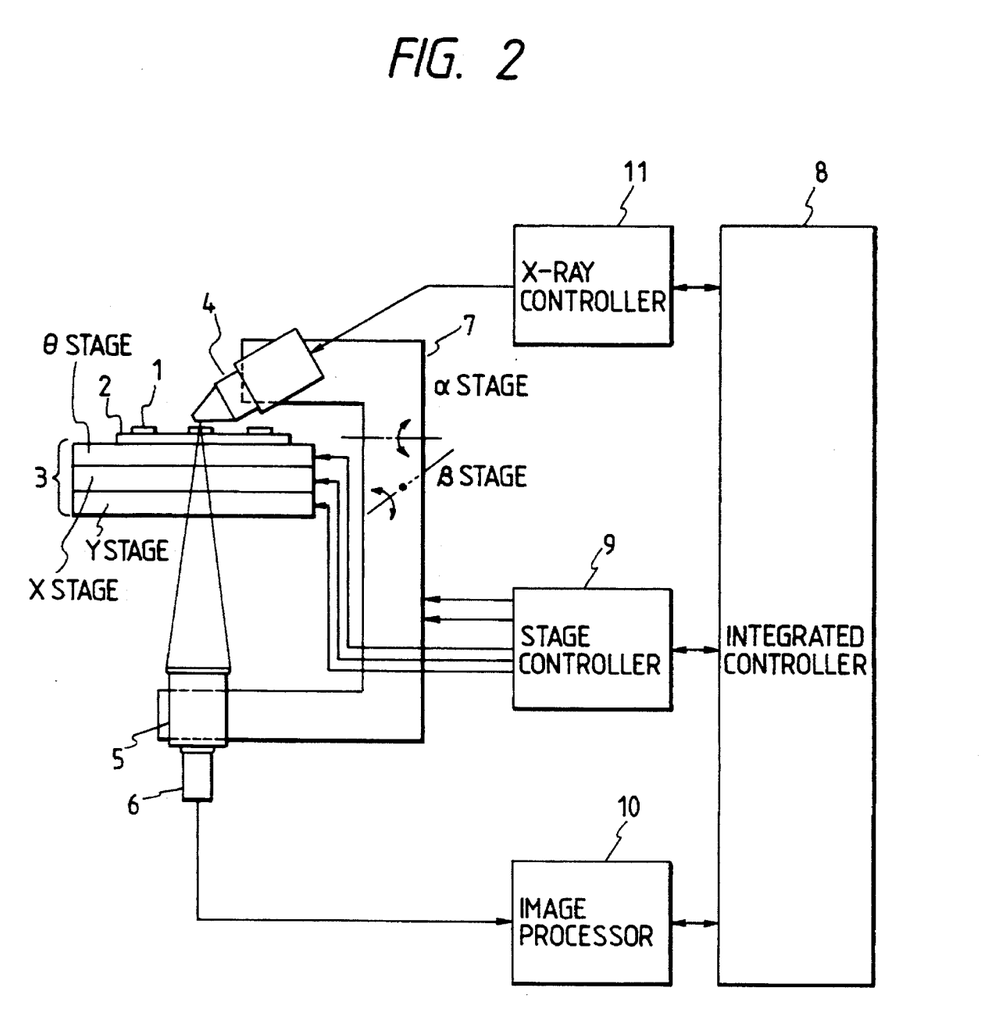
FIG. 2 is a schematic diagram for illustrating a generic composition of an inspection apparatus for soldered joints based on detecting an X-ray image.
Figure 3A:
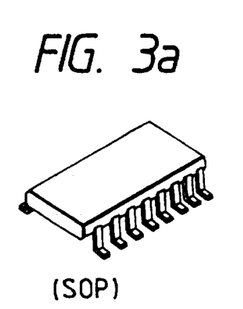
FIGS. 3a, 3b, 3c, 3d, and 3e are perspective illustrations for indicating representative examples of lead types for electronic parts (surface mounted devices) relating to the present invention.
Figure 3B:
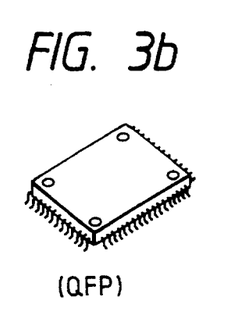
Figure 3C:
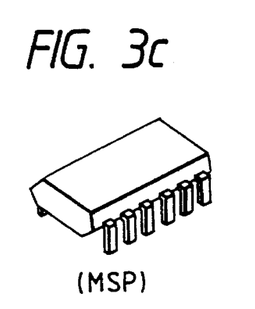
Figure 3D:
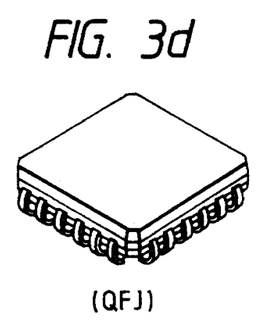
Figure 3E:
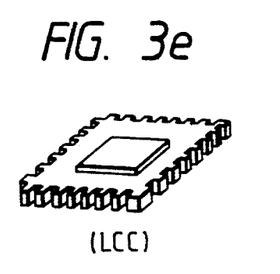
Figure 4A:
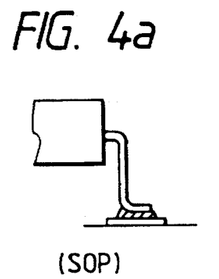
FIGS. 4a, 4b, 4c, and 4d are cross sections of soldered joints of the electronic parts shown in FIGS. 3a, 3d, 3c and 3e, respectively.
Figure 4B:
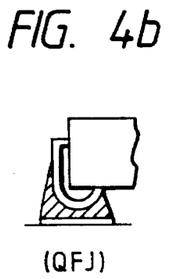
Figure 4C:
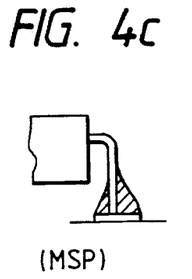
Figure 4D:
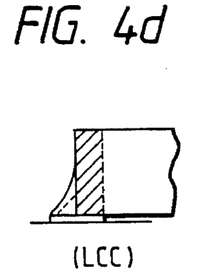

Referring to FIG. 2 which is a schematic diagram for illustrating a generic composition of an inspection apparatus for soldered joints using X-ray imaging, the present invention will be explained concretely.

As FIG. 2 indicates, an electronic part 1 is mounted on a surface of a printed circuit board 2 by soldering. The printed circuit board 2 is placed on a θXY stage 3 in order to be positioned at a predetermined location by being moved in X, Y directions and rotated in a horizontal plane. A micro focus X-ray source 4, an image intensifier 5, and a TV camera 6 are installed on an α β stage 7 having two rotational axes α, β which cross each other at a right angle. An X-ray image produced by an X-ray from the micro focus X-ray source 4 which is located in the vicinity of the printed circuit board 2 is detected and converted to an optical image by the image intensifier 5 which constitutes an X-ray image detector. The micro focus X-ray source 4 and the image intensifier 5 are maintained at fixed positions relative to each while they are rotated by the α β stage 7 to position an optical axis of the micro focus X-ray source 4 and the image intensifier 5 at a desired oblique angle with respect to soldered joints. The optical image is detected by the TV camera t as a two dimensional image signal. Inspection of the soldered joints is performed on the electronic part 1 which is mounted on the printed circuit board 2 by regulating an X-ray controller 11, a stage controller 9, and an image processor 10 with an integrated controller 8 which is composed of computers, etc. The X-ray controller 11 regulates voltage and current of an X-ray tube in the micro focus X-ray source 4, and generating and focusing of the X-ray, etc., depending on commands from the integrated controller 8. The stage controller 9 regulates the θXY stage 3 and the α β stage 7 depending on commands from the integrated controller 8 so that the X-ray irradiates desired soldered joints from a desired direction and an X-ray image of the soldered joints can be detected. The image processor 10 performs an image processing after receiving the two dimensional image signal from the TV camera 6 in accordance with commands from the integrated controller 8, and the integrated controller 8 decides whether a soldered joint is defective or not depending on a result from the above image processing. Whenever new soldered joints are inspected, the inspection of the soldering condition can be performed on each of the soldered joints in order by regulating the X-ray controller 11, the stage controller 9, and the image processor 10.

Some representative examples of various lead types of electronic parts (surface mounted devices) related to the present invention such as a Small Outline Package (SOP), a Quad Flat Package (QFP), a Mini Square Package (MSP), a Quad Flat J-leaded Package (QFJ), and a Leadless Chip Carrier (LCC) are shown in FIGS. 3a to 3e, respectively. FIGS. 4a to 4d indicate cross sections of soldered joints for the SOP, QFJ, MSP, and LCC packages, respectively. As the above figures reveal, all of the electronic parts are mounted on a surface of the printed circuit board by soldering the leads to the surface without inserting the leads into through-holes regardless of the lead types. The electronic parts having the lead types QFJ and LCC have shapes which make it possible to avoid superimposing the standing portion of their leads to on the solder portion in the X-ray image even if the X-ray is not projected obliquely to the standing portion of the leads. However, the electronic parts having the lead types SOP, QFP, and MSP have shapes which make it impossible to avoid superimposing the standing portion of their leads on the solder portion in the X-ray image obtained by the inspection method of the prior art. However, by applying the inspection method of the soldering condition of the present invention, the soldering condition can be determined clearly.

Taking the lead types SOP and QFP, both of which are gull wing types as examples, the present invention will be explained more concretely hereinafter.

(1) A case of one sided mounting

Figure 5:
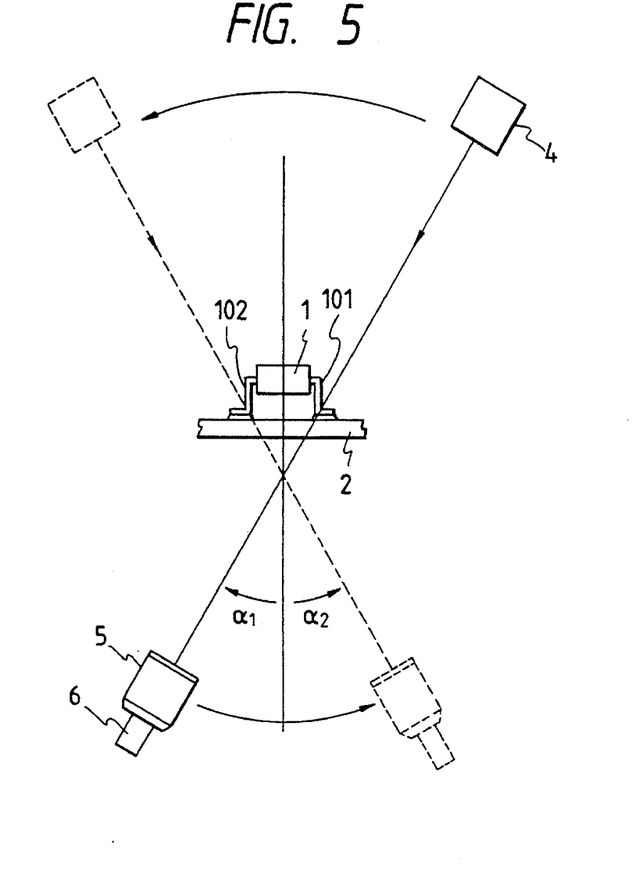
FIG. 5 is an illustration for explaining the inspection method for soldered joints relating to the present invention in a case when electronic parts are mounted on only one side of the substrate.

Referring to FIG. 2, the integrated controller 8 previously stores data on various parts, their lead positions, and inclination of the standing portions of the leads, etc., and based on the above data, the integrated controller 8 regulates each of the θXY stage 3 and the α β stage 7 through the stage controller 9 so as to inspect the soldering condition of the desired electronic part 1. In accordance with the above operation, the electronic part 1 is placed at a desired position in the vicinity of the micro focus X-ray source 4, the α stage is rotated to a desired angle $\alpha_1$ in a vertical plane about the α axis of the α β stage 7, and consequently, the inspection of the soldering condition of the electronic part becomes possible. An X-ray from the micro focus X-ray source 4 under the above condition can irradiate the standing portion of the lead 101 from an oblique direction as shown in FIG. 5.

Next, the integrated controller 8 regulates the X-ray controller 11 and the image processor 10 so as to detect the X-ray image with the image intensifier 5 and the TV camera 6 under a condition that the X-ray from the micro focus X-ray source 4 at a designated tube voltage and a designated tube current is projected to the lead 101. The detected X-ray image is processed in the image processor 10, and the integrated controller 8 determines whether the soldering condition of the soldered joint at the lead 101 is perfect or not based on the result obtained by the image processing in the image processor 10.

Subsequently, in order to inspect the soldered joint at the lead 102, the α stage is rotated in reverse to a desired angle $\alpha_2$ and the soldering condition at the lead 102 is inspected the same as in the case of the lead 101.

Figure 6:
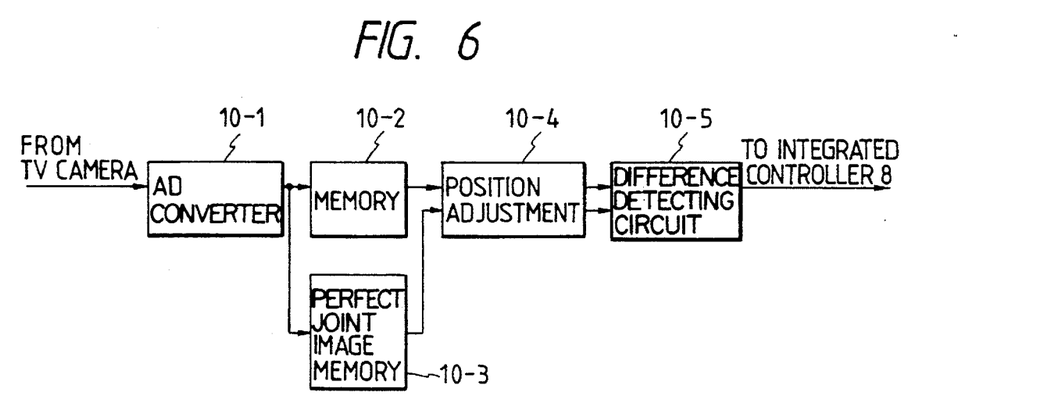
FIG. 6 is a diagram indicating an internal composition in an example of the image processor shown in FIG. 2.

Referring to FIG. 6, an internal composition of the image processor 10 will be explained hereinafter.

The two dimensional image signal from the TV camera 6 is converted to multivalue digital signals by an AD converter 10-1 and is stored temporarily in a memory 10-2 as a two dimensional image (including two dimensional images corresponding to a plurality of soldered joints), while, a two dimensional image for a perfect soldering condition is previously stored in a perfect joint image memory 10-3. By comparing the above two dimensional images at a same positioning condition, a judgement whether the soldering condition is perfect or not can be determined. As shown in FIG. 6, the positions of the two dimensional images from each of the memories 10-2 and 10-3 are adjusted to a same position by a position adjustment circuit 10-4 as a pre-processing step, and a difference image between the above two dimensional images at the same position can be obtained as a result of the comparison by a difference detecting circuit 10-5. The integrated controller 8 judges the soldering condition of the electronic part 1 to be defective when the difference image from the image processor 10 is larger than a predetermined threshold value.

In accordance with the above example, an actually detected X-ray image and a X-ray image for a perfect soldering condition which is actually detected or prepared by an appropriate method are compared with each other as a whole and a judgement whether any defect exists or not is performed for an electronic part unit. When a two dimensional image or a one dimensional image signal corresponding to only one of the soldered joints is extracted from the detected X-ray image and is compared with a two dimensional image or a one dimensional image signal for the perfect soldering condition at the soldered joint, the judgement can be performed for each of the soldered joints.

Figure 7:
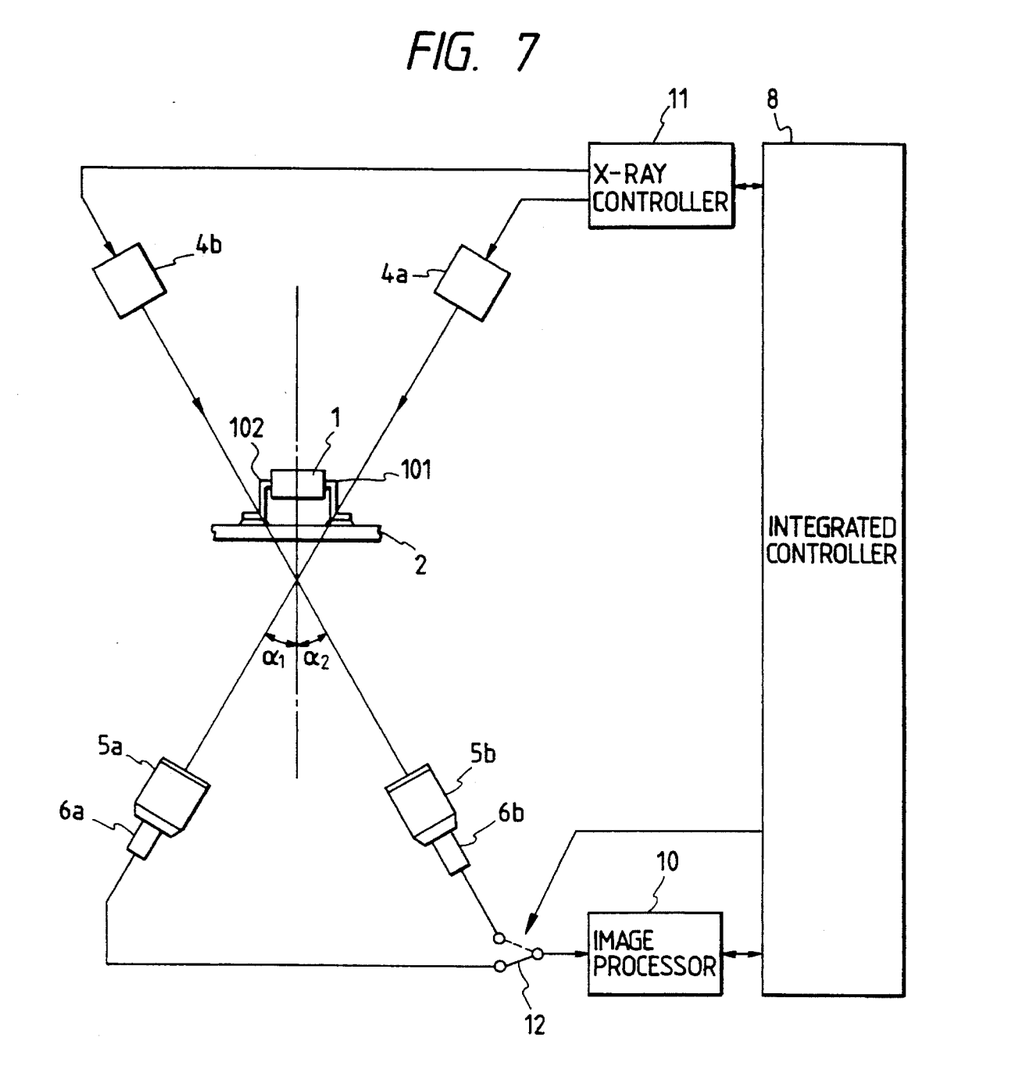
FIG. 7 is an illustration for indicating a fundamental composition of the inspection apparatus relating to the present invention for quick inspection of soldering conditions in a case when the electronic parts are mounted on only one side of the substrate.

Referring to FIG. 7, a fundamental composition of the inspection apparatus for quick inspection of the soldering condition in a case when the electronic parts are mounted on only one side of a substrate is illustrated. In accordance with the present example, two X-ray irradiation-detection systems are arranged on lines corresponding to aligning directions of the leads 101 and 102, respectively, that is, an X-ray irradiation-detection system comprising a micro focus X-ray source 4a, an image intensifier 5a, and a TV camera 6a are arranged on a line corresponding to the aligning direction of the lead 101 at an inclined angle of $\alpha_1$ relative to the standing portion of the lead 101, and an X-ray irradiation-detection system comprising a micro focus X-ray source 4b, an image intensifier 5a, and a TV camera 6b are arranged on a line corresponding to the aligning direction of the lead 102 at an inclined angle of $\alpha_2$ relative to a standing portion of the lead 102. Accordingly, when the lead 101 is selected for inspection, a selector switch 12 is connected to the TV camera 6a side, an X-ray from the micro focus X-ray source 4a is projected obliquely to the soldered joint of the lead 101, and the two dimensional image signal from the TV camera 6a is processed by the image processor 10. Subsequently, when the lead 102 is selected for inspection, the selector switch 12 is connected to the TV camera 6b side, an X-ray from the micro focus X-ray source 4b is projected obliquely to the soldered joint of the lead 102, and the two dimensional image signal from the TV camera 6b is processed by the image processor 10.

As explained above, when the X-ray irradiation-detection systems are previously arranged on lines corresponding to the aligning directions of the leads, the inspection for the soldering portion can be performed faster than in a case when only one X-ray irradiation-detection system is used.

(2) A case of two sided mounting

Figure 8:
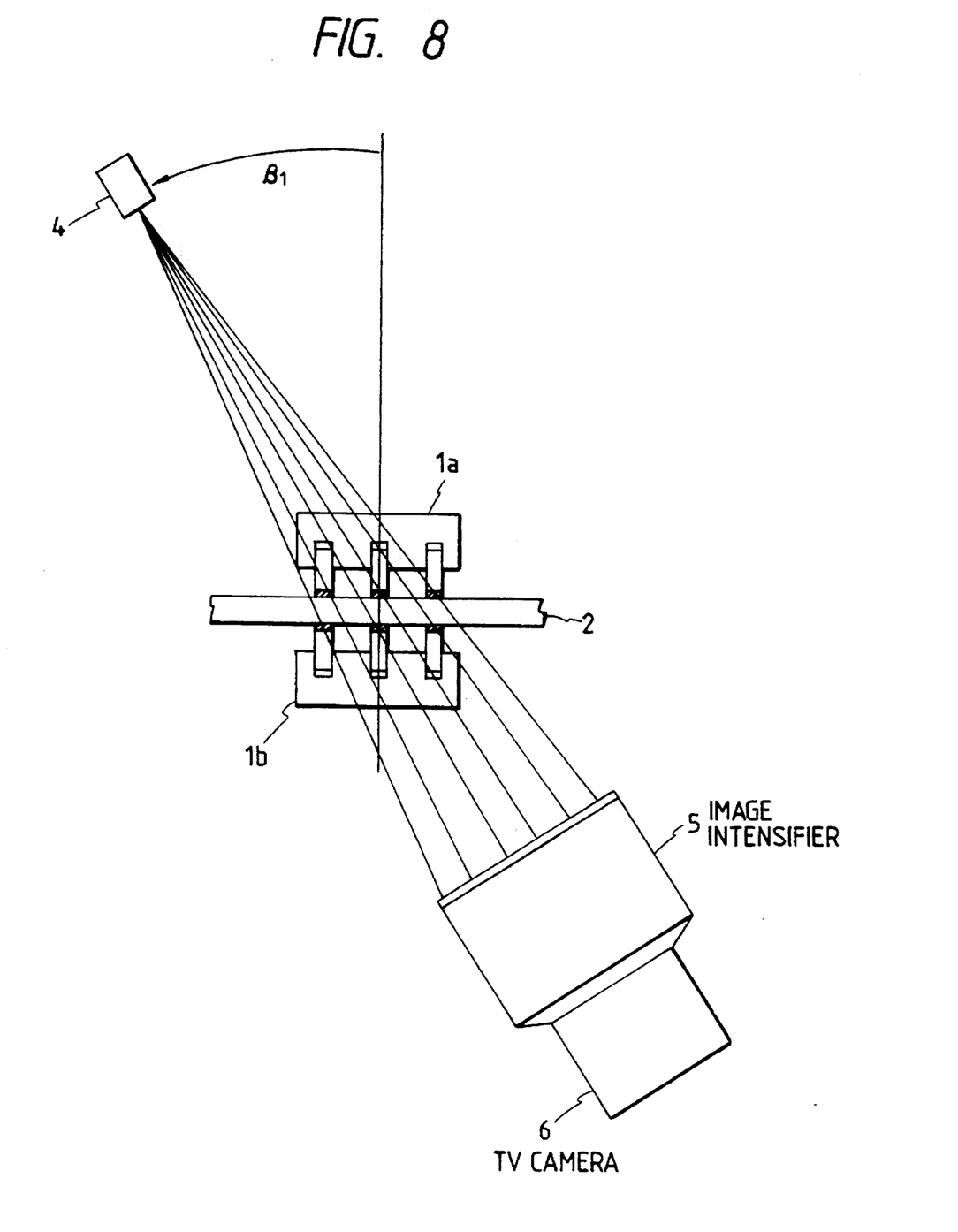
FIG. 8 is an illustration for explaining a position of a β stage in a case when electronic parts which are mounted on both sides of the substrate are inspected.
Figure 9:
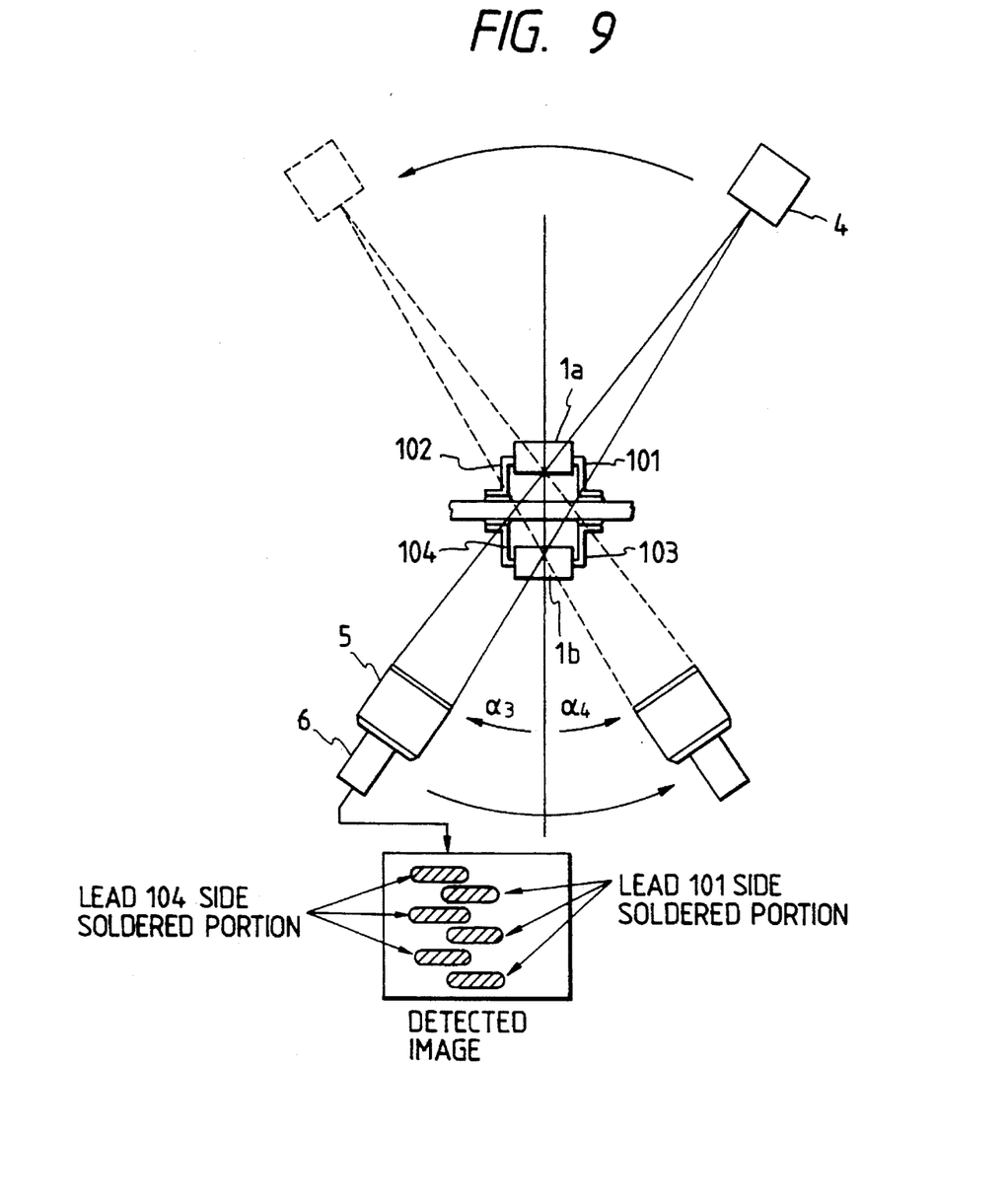
FIG. 9 is an illustration for explaining a position of an α stage in a case when electronic parts which are mounted on both sides of the substrate are inspected.

Referring to FIG. 2, the integrated controller 8 previously stores data on various surface mounted parts, reverse surface mounted parts, their lead positions, inclination of the standing portions of the leads, and thicknesses of the printed circuit board 2, etc., and based on the above data, the integrated controller 8 regulates each of the θXY stage 3 and the α β stage 7 through the stage controller 9 so as to inspect simultaneously the soldering conditions of two desired electronic parts 1a and 1b mounted back-to-back on opposite sides of the printed circuit board 2. As shown in FIG. 8, an X-ray from the micro focus X-ray source 4 can irradiate each of the soldered joints of electronic parts 1a and 1b simultaneously based on the same controlling as described above. At that time, as a result of rotation of the β stage by a desired angle $\beta_1$ in a vertical plane around the β axis, an optical axis of the X-ray irradiation-detection system is inclined at a predetermined angle in order to avoid superimposing images of the soldered joints of the electronic parts 1a and 1b. Next, as in the case of one sided mounting, the α stage is moved in order to each of positions having inclined angles $\alpha_3$ and $\alpha_4$ as shown in FIG. 9, and X-ray images are detected at each of the positions. Consequently, each of the X-ray images of the soldered joints of the leads 101 and 104 can be detected at the position having the inclined angle $\alpha_3$ and each of the X-ray images of the soldered joints of the leads 102 and 103 can be detected at the position having the inclined angle $\alpha_4$ with small effects of the standing portions of the above described leads.

As in two case of one sided mounting, when the X-ray irradiation-detection systems are previously arranged on lines corresponding to the aligning directions of the leads, the inspection of the soldered joints can be performed faster than in a case when only one X-ray irradiation-detection system is used.

Figure 10A:
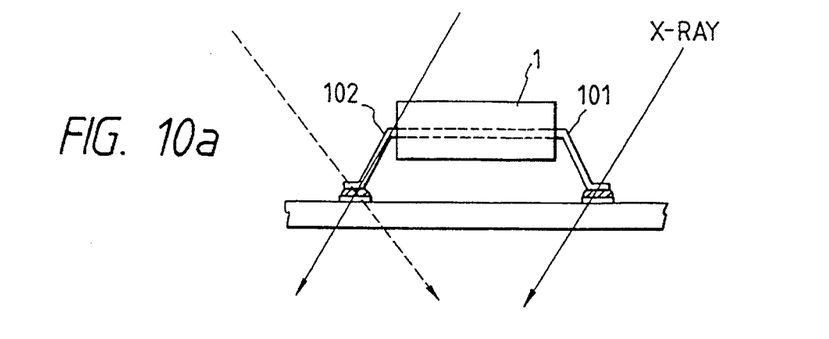
FIGS. 10a and 10b are illustrations for explaining the necessity of changing an irradiation angle depending on the type of the leads.
Figure 10B:
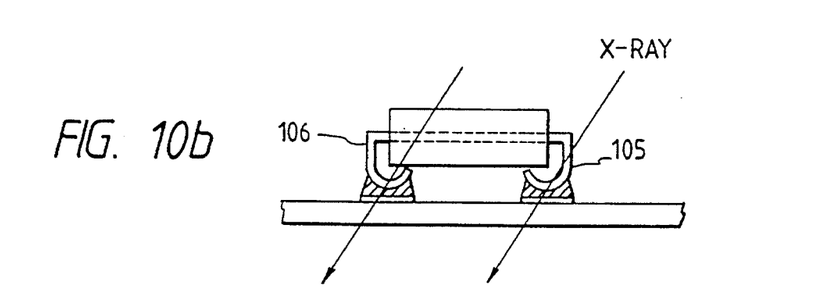

The present invention has been explained hitherto, but when the lead does not stand perpendicularly to the surface of the printed circuit board, an optimum X-ray irradiation angle α may be concretely determined individually by appropriate rotation of the α stage. Furthermore, depending on the lead types, the X-ray irradiation angle α is not necessarily altered. For example, the X-ray irradiation angle must be altered when the X-ray is projected from a direction as shown in FIG. 10a because a transmitting distance of the X-ray in the lead at the lead 102 side becomes long, while in such a case as shown in FIG. 10b, even if the X-ray is projected from only one direction, the transmitting distance of the X-ray in the lead at the lead 105 side does not differ very much from the distance at the lead 106 side, and accordingly, X-ray irradiation from only one direction is sufficient.

In accordance with the present invention as explained above, an inspection method for soldered joints using X-ray imaging which can determine a soldering condition of leads soldered to a surface of a substrate based on an X-ray image in a preferable condition is provided when electronic parts are mounted on the surface of the substrate by soldering to leads having a narrow pitch, and an apparatus therefor is also provided. Furthermore, an inspection method for soldered joints using X-ray imaging which can determine a soldering condition of leads soldered to a surface of a substrate in a short time based on an X-ray image in a preferable condition when electronic parts are mounted on the surface of the substrate by soldering to leads having a narrow pitch, and an apparatus therefor is also provided.

What is claimed is:

1. A method for inspecting a soldered joint with an X-ray, the soldered joint being formed by soldering a lead to a surface of a substrate, the method comprising the steps of:

moving the substrate so as to move the surface of the substrate in an XY plane to position the soldered joint at a desired position in the XY plane;

rotating the substrate so as to rotate the surface of the substrate in the XY plane to position the soldered joint at a desired orientation in the XY plane;

rotating an X-ray source and a detector about the soldered joint in both of two mutually perpendicular planes perpendicular to the XY plane while maintaining the X-ray source and the detector at fixed positions relative to each other to establish a desired oblique irradiation angle between an X-ray from the X-ray source and the lead on the surface of the substrate;

irradiating the soldered joint with the X-ray from the X-ray source at the desired oblique irradiation angle such that the X-ray is transmitted through the soldered joint and the substrate;

detecting the X-ray transmitted through the soldered joint and the substrate with the detector, the detector producing an output signal indicative of the detected X-ray; and determining a condition of the soldered joint based on the output signal of the detector.

2. An apparatus for inspecting a soldered joint with an X-ray, the soldered joint being formed by soldering a lead to a surface of a substrate, the apparatus comprising:

a θXY stage for moving the substrate so as to move the surface of the substrate in an XY plane to position the soldered joint at a desired position in the XY plane, and for rotating the substrate so as to rotate the surface of the substrate in the XY plane to position the soldered joint at a desired orientation in the XY plane;

an X-ray source for irradiating the soldered joint with an X-ray such that the X-ray is transmitted through the soldered joint and the substrate;

a detector for detecting the X-ray transmitted through the soldered joint and the substrate, and for producing an output signal indicative of the detected X-ray;

means for rotating the X-ray source and the detector about the soldered joint in both of two mutually perpendicular planes perpendicular to the XY plane while maintaining the X-ray source and the detector at fixed positions relative to each other such that the X-ray from the X-ray source irradiates the soldered joint at a desired oblique irradiation angle between the X-ray and the lead on the surface of the substrate; and means for determining a condition of the soldered joint based on the output signal of the detector while the X-ray irradiates the soldered joint at the desired oblique irradiation angle.

3. An apparatus according to claim 2, further comprising means for producing an X-ray fluoroscopic image based on the output signal of the detector.

4. A method for inspecting a soldered joint with an X-ray, the soldered joint being formed by soldering a lead to a surface of a substrate, the method comprising the steps of:

moving the substrate so as to move the surface of the substrate in an XY plane to position the soldered joint at a desired position in the XY plane;

rotating the substrate so as to rotate the surface of the substrate in the XY plane to position the soldered joint at a desired orientation in the XY plane;

sequentially selecting each one of a plurality of X-ray source/detector systems, each of the X-ray source/detector systems including an X-ray source and a detector disposed at fixed positions relative to each other;

rotating the X-ray source and the detector of the selected X-ray source/detector system about the soldered joint in both of two mutually perpendicular planes perpendicular to the XY plane while maintaining the X-ray source and the detector of the selected X-ray source/detector system at the fixed positions relative to each other to establish a desired oblique irradiation angle between an X-ray from the X-ray source of the selected X-ray source/detector system and the lead on the surface of the substrate;

irradiating the soldered joint with the X-ray from the X-ray source of the selected X-ray source/detector system at the desired oblique irradiation angle such that the X-ray is transmitted through the soldered joint and the substrate;

detecting the X-ray transmitted through the soldered joint and the substrate with the detector, the detector producing an output signal indicative of the detected X-ray; and determining a condition of the soldered joint based on the output signal of the detector.

5. An apparatus for inspecting a soldered joint with an X-ray, the soldered joint being formed by soldering a lead to a surface of a substrate, the apparatus comprising:

a θXY stage for moving the substrate so as to move the surface of the substrate in an XY plane to position the soldered joint at a desired position in the XY plane, and for rotating the substrate so as to rotate the surface of the substrate in the XY plane to position the soldered joint at a desired orientation in the XY plane;

a plurality of X-ray source/detector systems, each of the X-ray source/detector systems including an X-ray source and a detector disposed at fixed positions relative to each other, the X-ray source being for irradiating the soldered joint with an X-ray such that the X-ray is transmitted through the soldered joint and the substrate, and the detector being for detecting the X-ray transmitted through the soldered joint and the substrate, and for producing an output signal indicative of the detected X-ray;

means for sequentially selecting each one of the X-ray source/detector systems;

means for rotating the X-ray source and the detector of the selected X-ray source/detector system about the soldered joint in both of two mutually perpendicular planes perpendicular to the XY plane while maintaining the X-ray source and the detector of the selected X-ray source/detector system at the fixed positions relative to each other such that the X-ray from the X-ray source of the selected X-ray source/detector system irradiates the soldered joint at a desired oblique irradiation angle between the X-ray and the lead on the surface of the substrate; and means for determining a condition of the soldered joint based on the output signal of the detector while the X-ray irradiates the soldered joint at the desired oblique irradiation angle.

6. An apparatus according to claim 5, wherein the X-ray source and the detector of each of the X-ray source/detector systems are disposed at fixed positions relative to each on a respective irradiation axis, and wherein the respective irradiation axes of the X-ray source/detector systems are mutually different from each other.

* * * * *